Aug. 10, 1971 H. W. GUENGERICH Plant Pat. 3,058
APPLE TREE
Filed Aug. 27, 1969
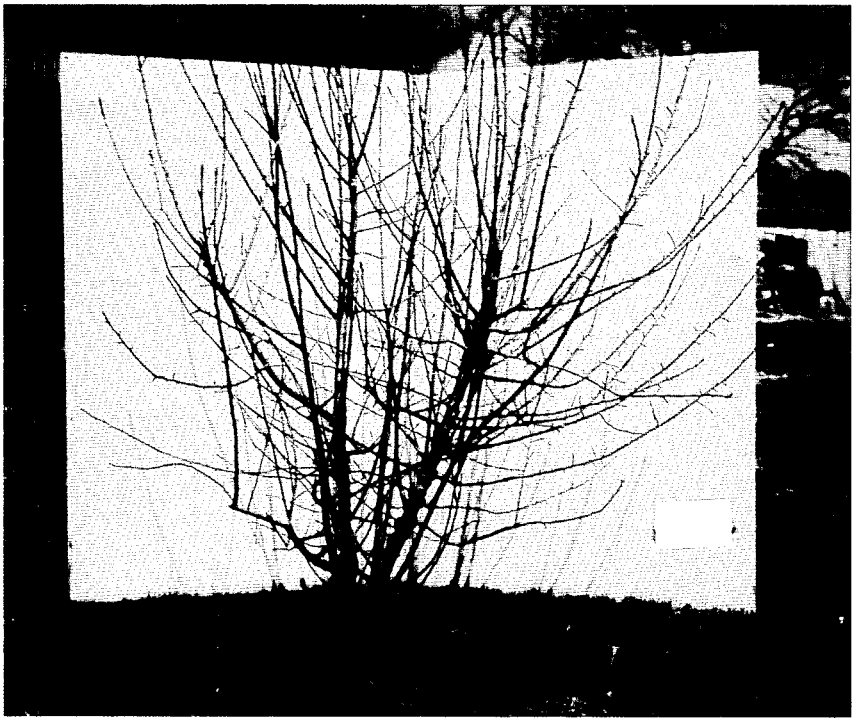
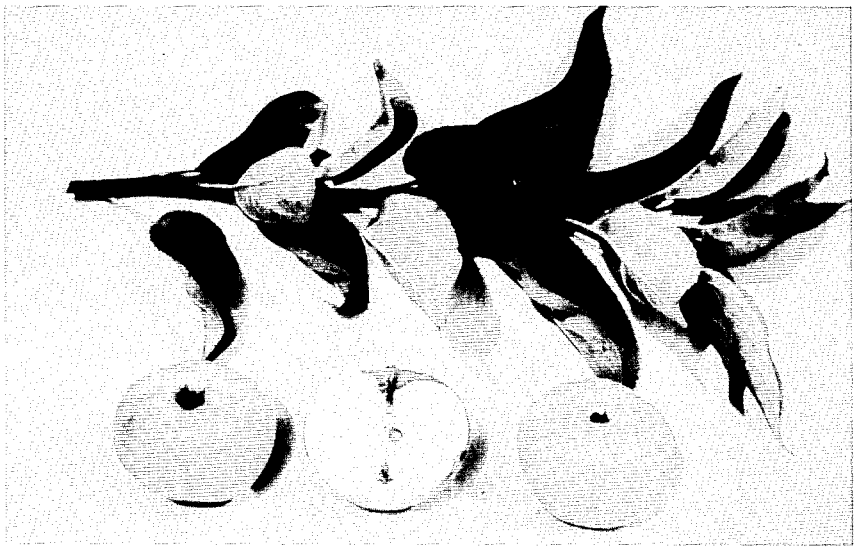
Inventor.
H. W. Guengerich
By: Robb & Robb
Attorneys.

United States Patent Office

Plant Pat. 3,058
Patented Aug. 10, 1971

3,058
APPLE TREE

Harry W. Guengerich, Louisiana, Mo., assignor to Stark Bro's Nurseries & Orchards Company, Louisiana, Mo.

Filed Aug. 27, 1969, Ser. No. 853,555
Int. Cl. A01h *5/03*
U.S. Cl. Plt.—34 1 Claim

The present invention relates to a new and distinct variety of apple tree which was discovered by me in a test orchard owned by my assignee and located near Louisiana, in Pike County, Mo., said new variety having originated as an open-pollinated seedling of the variety of apple tree known as "Clark Dwarf" (unpatented).

My new discovery resulted from a research program conducted by my assignee under my direction, and had for its primary objective the development of a new and improved variety of apple tree which would be useful as dwarfing interstock for producing dwarf apple trees having improved characteristics as compared with those produced by an unnamed and unpatented dwarfing interstock known as "EM VIII" which formerly was extensively used by my assignee, but which is susceptible to stem-pitting virus. This objective was fully achieved, as evidenced by the fact that, as a tree, it is taller and less spreading than "EM VIII," but is more tolerant to stem-pitting virus. Also, when the new variety is used as dwarfing interstock, it produces trees that are somewhat larger than trees derived from the use of "EM VIII" as dwarfing interstock, that is, about three quarters of the size of standard trees grown on the usual seedling rootstock, but which bear heavily and at an earlier age. All of these attributes are commercially valuable.

Asexual reproduction of my new variety by layering, as performed by me in Pike County, Mo., shows that the foregoing characteristics and distinctions come true and are established and transmitted through succeeding propagations.

The accompanying drawing shows a typical bare tree of my new variety, as well as typical specimens of its foliage and fruit, with one of the fruit specimens being shown in longitudinal cross-section, and all as depicted in color as nearly true as it is reasonably possible to make the same in a color illustration of this character.

The following is a detailed description of my new variety, with color terminology in accordance with Ridgway's Color Standards and Nomenclature, hereinafter abbreviated as R, and Horticultural Colour Guide, hereinafter abbreviated as HCG, except where general color terms of ordinary dictionary significance are obvious:

Location where grown and observed: Pike County, Mo.
Dates of first and last pickings: About July 28 and August 10, respectively.

Tree: Medium small and bushy, but about twice the size of "EM VIII"; vigorous; upright-spreading; low, but about twice the height of "EM VIII"; dense; vase-formed; rapid growing; hardy; medium productive; uncertain bearer.

*Trunk.*—Medium slender; shaggy.

*Branches.* — Medium slender; smooth; much-branched. Color (shoots)—Dark Vinaceous Brown, Plate XXXIX, Color No. 5‴, tone k (R).

*Lenticels.*—Medium numerous; medium small.

*Leaves.*—Medium large; medium wide; medium short; ovate; taper-pointed; thick; rugose. Length—From about 2½ inches to 3 inches. Width—From about 1¾ inches to 1⅞ inches. Color—Parsley Green, Plate 00962/1, page 193, volume II (HCG). Margin—Coarsely serrate. Petiole—Medium long; medium slender.

Flowers: Medium early.

*Dates of first and full bloom.*—About April 19 and April 27, respectively.

*Size.*—Medium large.

*Color.*—White, with pink tinge near margins of some petals.

Fruit:

*Maturity when described.*—Eating ripe (about August 7).

*Size.*—Variable. Axial diameter—From about 1¾ inches to 2 inches. Transverse diameter—From about 2¼ inches to 2½ inches.

*Form.*—Oblate at base; ribbed.

*Cavity.*—Unsymmetrical; rounded toward apex; acute; undulate. Depth—About 5/16 inch. Breadth—about 1⅛ inches. Markings—Russetted Old Gold, Plate XVI, Color No. 19′, tone i (R).

*Basin.*—Symmetrical; abrupt at base; narrow; undulate; pubescent. Depth — About ¼ inch. Breadth—About 1 inch. Markings—None.

*Stem.*—Medium stout; pubescent. Length—From about ¾ inch to ⅞ inch. Breadth—About 1/16 inch. Markings—None.

*Calyx.*—From open to closed; segments persistent; broadly lanceolate; acute; about ¼ inch long; separated; prostrate; converged from base toward center; connivent; pubescent on both outer and inner surfaces.

*Skin.*—Tough; smooth; glossy; waxed. Dots—Obscure; few; small; raised; ruptured; circular. Color—Cacao Brown, Plate XXVIII, Color No. 9″, tone i (R). Distribution—Most numerous toward calyx end. Ground color—Primrose Yellow, Plate 301/2, page 65, volume I (HCG). Color markings—Blushed; bright. Color—Claret Rose, Plate 021, page 109, volume II (HCG). Bloom—Moderate. Scarfskin—Wanting.

*General color effect.*—Bright red, with greenish-yellow ground color.

*Flesh.*—Rather dry. Color—White with greenish tint. Texture—Hard; tough; fine; crisp. Flavor—Sweet. Aroma—Wanting. Quality—Inferior.

*Core.*—Median. Bundle area—Medium large; broadly ovate; symmetrical at base. Halves of core—Equal. Bundles—Inconspicuous; in one whorl. Color—Green. Core lines—Clasping. Cross section — Indistinct. Carpellary area — Indistinct; small.

Calyx tube—Glabrous; broadly cone-shaped. Entire depth—About ⅜ inch.

*Styles.*—Present; united toward base; pubescent toward base.

*Stamens.*—In one obscure whorl; marginal.

*Seed cells.*—Abasile; closed. Cell walls—Approximate; thick; tough. Length—About ½ inch. Breadth—About 5/16 inch. Longitudinal section—

Orbicular; obtuse at apex. Surface—Entire; smooth. Cross section—Narrow.

Seeds:

*Average number.*—From 5 to 7 perfect; 2 per cell.

*Length.*—About 5/16 inch.

*Breadth.*—About 7/32 inch.

*Form.*—Acute.

*Color.*—Liver Brown, Plate XIV, Color No. 7′, tone m (R).

Use: Fruit worthless, but woody stems useful as good dwarfing interstock.

Disease resistance: Good tolerance to stem-pitting virus, as determined from comparison with other varieties grown under comparable conditions in Pike County, Mo.

I claim:

1. A new and distinct variety of apple tree, substantially as herein shown and described, characterized particularly as to novelty by a taller and less spreading tree habit than the variety identified as "EM VIII" formerly used extensively as dwarfing interstock, and having greater tolerance to stem-pitting virus than "EM VIII," said new variety also having superior utility as dwarfing interstock to produce dwarf apple trees about three-quarters the size of standard trees grown on the usual seedling rootstock, but which bear heavily and at an earlier age.

No references cited.

ROBERT E. BAGWILL, Primary Examiner